United States Patent
Smith (10) Patent No.: US 7,346,174 B1
(45) Date of Patent: Mar. 18, 2008

(54) MEDICAL DEVICE WITH COMMUNICATION, MEASUREMENT AND DATA FUNCTIONS

(76) Inventor: Clive Smith, 6571 S. Pontiac Ct., Englewood, CO (US) 80111

( * ) Notice: Subject to any disclaimer, the term of this patent is extended or adjusted under 35 U.S.C. 154(b) by 0 days.

(21) Appl. No.: 09/412,140

(22) Filed: Oct. 5, 1999

Related U.S. Application Data (60) Provisional application No. 60/103,018, filed on Oct. 5, 1998.

(51) Int. Cl.
   *A61B 7/04* (2006.01)
(52) U.S. Cl. .......................... 381/67; 181/131; 600/528
(58) Field of Classification Search ................. 381/67; D24/165; 600/528; 181/131, 135
   See application file for complete search history.

(56) References Cited

U.S. PATENT DOCUMENTS

| | | | | |
|---|---|---|---|---|
| 4,320,767 A | * | 3/1982 | Villa-Real | 600/493 |
| 5,010,889 A | * | 4/1991 | Bredesen et al. | 600/528 |
| 5,457,751 A | * | 10/1995 | Such | 381/375 |
| 5,825,895 A | * | 10/1998 | Grasfield et al. | 381/67 |
| 5,880,452 A | * | 3/1999 | Plesko | 235/472.01 |
| 6,022,315 A | * | 2/2000 | Iliff | 600/300 |
| 6,236,862 B1 | * | 5/2001 | Erten et al. | 455/501 |
| 6,261,238 B1 | * | 7/2001 | Gavriely | 600/532 |

* cited by examiner

*Primary Examiner*—Vivian Chin
*Assistant Examiner*—Con P. Tran
(74) *Attorney, Agent, or Firm*—Coun P. Abrahams (57) ABSTRACT

A medical diagnostic and communications apparatus with audio output comprises an electronic processor for processing stethoscope signals and secondary audio signals. An electronic stethoscope sensor is contained within a housing for transducing body sounds to electronic signals, and is operatively connected to the electronic processor. One or more secondary audio signal sources operatively connects to the electronic processor. A common audio output is connected to electronic processor to convert electronic stethoscope signals or secondary audio signals to acoustic output. These sounds may be produced separately or mixed.

11 Claims, 5 Drawing Sheets

SIDE VIEW

FRONT VIEW

FIGURE 1
SYSTEM/DEVICE BLOCK DIAGRAM

FIGURE 2
AUSCULTATION ALTERNATE-SOURCE AUDIO MIXER

FIGURE 3

FRONT VIEW

SIDE VIEW

FIGURE 5
COMMUNICATIONS AND DATA ACCESS METHODS

MEDICAL DEVICE WITH COMMUNICATION, MEASUREMENT AND DATA FUNCTIONS

CROSS REFERENCE TO RELATED APPLICATIONS

This application claims the benefit of U.S. Provisional Application No. 60/103,018 filed Oct. 5, 1998.

FIELD AND BACKGROUND OF THE INVENTION

The present invention relates to a medical communications, information and measurement device with multiple functions built into the same unit, to produce a portable device. The preferred embodiment is in the form of a stethoscope-like device with expanded, general-purpose medical measurement, information and communications functions, beyond the basic auscultation functions. However the invention is not restricted to such a configuration, and may also be built in the form of an information and communications device without sensing or measurement capability. The invention can also be built in a form suited to other work environments outside the medical field, where the combination of functions is also beneficial. The invention also covers methods for accessing medical and other information and digital data via a portable device. The benefits of the invention relate to the integration of digital wireless communications and information access in the work environment, using user-friendly interface methods, in order to make information retrieval, information management, and communications an integral part of work process.

A problem encountered by medical workers is that many measurement and information means used in their work are not portable, or are inconvenient to integrate into the work flow, requiring the worker to divert attention from the patient or move from the patient bedside to access the information or measurement means. Computers are provided for patient and medical information, but these are usually fixed in specific locations. When such means are portable, they are embodied in discrete devices which are single-purpose, rather than being embodied in a convenient, combined or integrated means for use and portability. For example, a pager is convenient to carry, but provides only a single function. The same applies to cell phones, stethoscopes, blood pressure cuffs, oximeters, and nonmechanical information devices such as books, journals and reference materials. All of these devices are discrete, and single-purpose, and require the worker to carry multiple devices or use differing means for accessing information, making measurements or performing communications and recording tasks.

Stethoscopes are carried by almost every physician, nurse or medical worker during working hours. Stethoscopes have been limited to specific functions—primarily auscultation and blood pressure measurement. The majority of stethoscopes are mechanical devices, however a number of electronic versions have been reported, with some communications capability, limited to the transmission of auscultation sounds via infrared or telephone. Some electronic stethoscopes have included some additional measurement capability, such as heart rate or time interval measurements.

However, the transition from a mechanical to an electronic stethoscope introduces the potential to expand the functionality of the stethoscope, using it as a more general-purpose electronic platform for other functions that are useful to the medical worker. The form factor of the stethoscope allows it to be worn comfortably around the neck or shoulders, and the audio input and output functions can be used for other applications beyond auscultation. The fact that it is carried around so extensively in the medical setting makes it an ideal platform for many additional functions of an electronic nature.

While the descriptions herein describe the use of the invention in a medical setting, the invention is not limited to medical applications. The same combination of elements described herein may be used in various other applications. While then preferred embodiment includes a stethoscopes function, other embodiments of the invention may include other elements of the invention, and omit the stethoscope function. The underlying structure of the invention, and the methods associated therewith, concern the advantages obtained by combining various elements to form a system that is easier to use and provides new functions and methods as part of the work flow, that were not previously practical or simple.

SUMMARY OF THE INVENTION

The present invention addresses the problem of multiple devices in the workplace, and exploits the potential for a unified electronic platform with integrated digital functions, by embedding different functions into a single device. The preferred embodiment is in the form of a stethoscope to be used in the medical work environment. A key innovation is the transformation of the stethoscope into a multiple-use device. In a more general sense, the benefit of the invention is to bring information, measurement and communications technology into the work flow. This is especially of value in medicine, where the use of computers and other electronic equipment, especially of an informational and data processing nature, is a diversion from the patient or the bedside.

Stethoscopes have been reported that have infrared communications, PC communications, and telephonic communications. However, the purpose of these links is primarily to transfer auscultation information i.e. for remote listening or recording of sounds. The present invention goes beyond these limitations to include new communications, storage and processing functionality, for the transfer, storage and processing of data besides auscultation sounds, and the local storage of data and information that is of a more general nature. Examples of such information include, but are not limited to; patient records including but not limited to patient history, sounds and images; pharmaceutical databases including but not limited to drug dosage and drug interactions; medical research information including but not limited to reference sounds, diagnoses, images, and research results; insurance claim, policy and benefit information; and billing information. These data can be stored locally on the device, or communicated via the communications links embedded in the invention. The communications capability includes, but is not limited to, wireless, infrared, and cabled connections to telephones, telephone systems, computer networks, and the Internet.

Finally, the user interface of the present invention introduces novel features and methods not previously associated with stethoscopes or information access and communications devices in general, including voice recognition, speech recognition, data-to-speech, text-to-speech, and audio prompting. Such user-friendly interfacing is a key innovation for a portable device, where small keyboards and pen input have been the rule.

When the embodiment excludes the stethoscope function, the invention may comprise other elements for medical and other information communications, storage and processing. The invention then provides the worker with convenient user interface, communications and processing capability.

The invention comprises both a device, or physical embodiment, and methods associated with the use of the device in a wider system.

DETAILED DESCRIPTION OF THE PREFERRED EMBODIMENTS

The invention consists of a device comprising a number of sub-systems, with each sub-system comprising certain elements, which are operationally connected. The uniqueness of the invention does not require that all sub-systems and elements exist together in the device, since the invention may comprise a subset of the elements described herein. Beyond an actual device, the invention also includes methods, such methods being steps for processing signals, data and information. Those aspects of the invention that comprise methods, typically include the device as an integral part of the method i.e. the device is used in conjunction with other devices (such as computers or telecommunications systems), using a sequence of steps, to form an original procedure or method.

Figure 1:
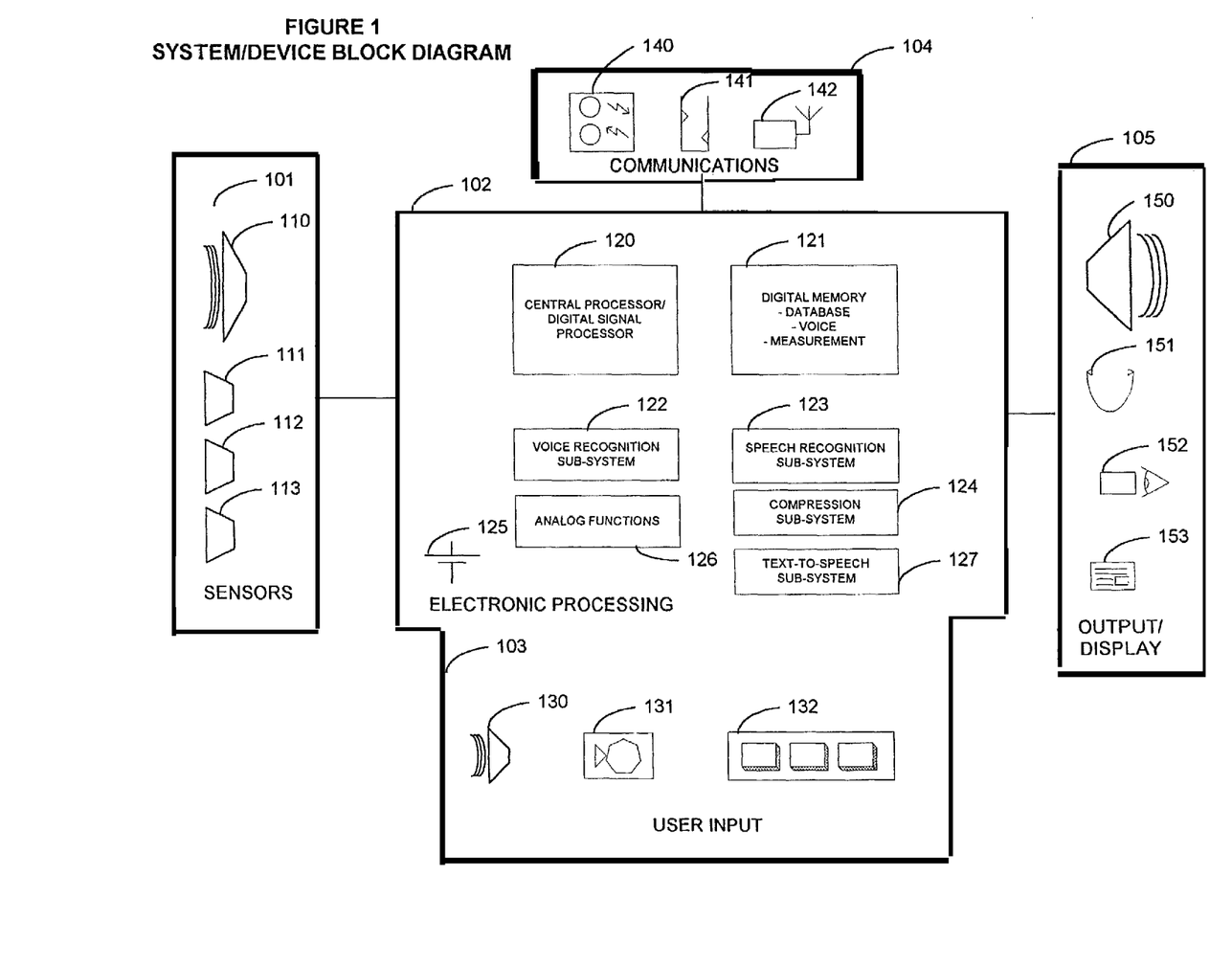
FIG. 1 is a block diagram of the major functions and sub-systems of the device of the invention.

The major sub-systems of the device, as shown in FIG. 1 are:

(a) A Sensor sub-system (101).

(b) An Electronics Processing sub-system (102).

(c) A User Input sub-system (103).

(d) A Communications sub-system (104).

(e) An Output/Display sub-system (105).

The sub-systems and their elements are:

Sensor Sub-System 101:

The Sensor sub-system 101 comprises one or more of the following elements:

(a) Stethoscope sensor 110, to sense body sounds.

(b) Pulse Oximetry sensor 111 to sense blood oxygen level.

(c) Temperature sensor 112 to detect body temperature.

(d) One or more additional sensors (113) to sense other measurements. All of these sensors have in common the capability to make measurements of external phenomena of a physical or physiological nature. Examples include electrocardiography electrodes, glucose measurement means, an ultrasound probe, a video camera or a barcode scanner for reading labels.

One or more of the above sensors is operationally connected to the electronics processing sub-system 102 and sensed measurements are transferred to the Electronics Processing sub-system 102 for further processing. In the preferred embodiment, the stethoscope or auscultation sensor is present, however this may be replaced be another sensor, used in addition to other sensors, or the sensor sub-system may be absent, making the invention an information and/or communications device without sensing capability.

User Input Sub-System 103:

The User Input sub-system 103 provides the operator with control of the electronics processing subsystem 102. This may be done via a plurality of control means. Specifically, the User Input sub-system consists of one or more of the following elements:

(a) Microphone 130 for voice input. This microphone is distinct from the stethoscope microphone and is used for voice input from the user in the preferred embodiment. However, the microphone may be the same device used for auscultation.

(b) Rotary thumbwheel 131, with optional built in push-button mechanism. In the preferred embodiment, the rotary device is a digital input device which produces pulses in conjunction with additional or embedded circuitry when rotated, but an analog potentiometer may also be used. In the case of the digital thumbwheel, the wheel may be rotated through 360 degrees. Inputs from the rotary device are correlated with control or menu selections. As the rotary device is actuated, feedback may be provided to the user via audio output or spoken voice to confirm a selection.

(c) Keypad, touchscreen or individual buttons 132.

The above input devices allow the user to enter voice information or commands, use a rotary switch for volume, menu selections or other entries, or push buttons, pen or touch to enter selections. The preferred embodiment includes one or more of these control methods.

The microphone is used for voice or speech input. Voice or speech input is used in the following manner, and becomes an integral part of the steps that form many of the methods of the invention:

Voice is recorded as raw or compressed sound signals, for later transmission, storage, or transcription, such as for medical record-keeping. Voice recognition is performed, for the purposes of user identification. Voice signals are processed and recognized in the device itself, using software and data within the device, or voice may be pre-processed, and voice recognition performed by a remote system. A remote system is defined as a system that is not part of the device, and with which the device communicates via the Communications sub-system. Thus remote voice recognition comprises the steps of recording the voice digitally, optionally pre-processing the sounds, transmitting the signal digitally to a remote system, the remote system containing voice recognition means. The results are then transmitted back to the device.

To perform speech recognition, for the purposes of control and data entry. The speech sounds are processed locally or in a remote system, being converted to commands or data, either locally or remotely. The method is analogous to the voice recognition process, except that semantics (meaning, commands or data) are derived from the speech signal.

Electronic Processing Sub-System 102:

The Electronic Processing sub-system 102, provides hardware, firmware, software and storage functionality, and is operationally connected to the Sensor subsystem 101, User Input sub-system 103, Communications sub-system 104, or Output/Display sub-system 105. The Electronic Processing sub-system consists of one or more of the following elements:

(a) Central Processor/Digital Signal Processor 120, which controls the system and processes data, measurement signals and information. The central processor may optionally include means for going into a standby power-saving mode or low clock-speed mode, although this is not required for the invention to operate.

(b) Digital Memory 121, which stores programs (software), voice information, voice recordings, medical data, databases, measurements, reference measurement information, reference voice information, and other data necessary for system operations. Specifically, the data stored may include voice recognition data to identify the user or owner of the device; speech recognition data to identify voice commands so that the device may respond to voice commands; data-to-speech and text-to-speech tables and data in order to convert data and text to speech output; patient data including auscultation sounds, patient history, patient image data; pharmaceutical data including dosage data or drug interaction data; medical research statistics and information to assist the medical worker with diagnosis and treatment by providing such data on a realtime basis; scheduling information for appointments and time management; insurance data regarding reimbursement for specific insurance plans, reimbursements and recommended or approved procedures for given diseases; billing information and storage; and other data relevant to the treatment of patients and management of medical information. Algorithms may be included in the memory for various diagnostic functions and signal analysis functions. The digital memory may be split into discrete units so that various data types are stored in specific memories, or the memory may be a single device. The memory used for storage of reference information is of a nonvolatile nature or is battery-backed. Nonvolatile technologies include but are not limited to Flash, EEPROM, or magnetic media. The memory may be fixed or removable. The memory may contain both data and program code related to the access and processing of the abovementioned data and information types.

(c) Voice recognition sub-system 122, which provides security features to validate the user's identity to avoid theft or unauthorized access to information. The voice recognition function is implemented as a hardware, firmware or software function. The voice recognition function may optionally include the use of the Communications sub-system 104 of the invention in order to access voice verification data from a remote site. In this case, the raw voice, or a pre-processed version of the voice data may be transmitted between the remote site and the invention.

(d) Speech Recognition sub-system 123, which processes signals from the microphone in order to perform database searches, respond to commands, store information, or perform speech-to-text transcription either within the device or remotely via the Communications sub-system 104 provided in the invention.

(e) Compression sub-system 124 which compresses signals, voice or data to provide efficient storage in the Digital Memory 121 and/or efficient information transfer via the Communications sub-system 104. The Compression sub-system also includes the capability to de-compress or expand the stored or received data.

(f) Battery power supply 125, to provide power to all sub-systems in a portable manner. The supply optionally includes power management functions to perform power conservation functions, including sensing of active use or idle time to determine power states.

(g) Analog Functions 126, including audio input, filtering, amplification, and output.

(h) Text-to-Speech system 127 converts stored or received data into speech for audio reproduction. This includes a data-to-speech function for converting data or measurements to speech output.

Many of the above functions can be implemented in hardware, or software residing in the memory 121, and processed by Processor 120. The invention does not need all of the above features to be functional, but uses one or more of the above in the invention. FIG. 1 shows the elements in schematic form. Their implementation may be in the form of hardware, software, or firmware, and their relationship may be of a software nature, via a central software operating system residing in the system.

Communications Sub-System 104:

The Communications sub-system 104, provides digital communications to like devices, to computers, to computer networks, to the telephone system, to the Internet, or to a large external communications network. There are 3 modes of communications provide for, and any one of these is included in the invention:

(a) Infrared Link 140, which provides wireless communication. An industry-standard infrared link such as IRDA is likely to be used, however any communications protocol may be implemented.

(b) Wired connection via a connector 141, to provide wired communications.

(c) Radio communications 142 to provide communications functions. The radio can implement any one of a number of radio protocols and functions, including pager functions, cellular communications, spread spectrum communications, or digital network protocols. These protocols may include PCS, CDMA, TDMA, IEEE 802.11, the Flex pager protocol, or digital satellite communications. Wireless communications using satellite communications protocols is also anticipated by this invention. In a home environment, the wireless channel may additionally be implemented by a 900 MHz digital communications scheme or other domestic wireless protocol. It is to be understood that this list does not limit the various methods that may be used.

Software in the Electronics Processor or the Communications sub-system itself controls the operations of the communications channel. This includes software protocols including, but not restricted to, TCP/IP, PPP, FTP, or other Internet protocols.

The communications function is not critical to all operations of the device, but provides unique capability to exchange information with other systems. The Communications sub-system is intended to provide information exchange beyond auscultation information, for broader medical data purposes. The data types include, but are not limited to, any of the data stored in the Digital Memory, and described under the Digital Memory section. In addition, the communications links may be used for regular voice communications of a telephonic or conversational nature, to provide partial or complete wireless telephone functions. The communications capability further includes the ability to locate the device logically or physically, to aid in the location of a medical worker, such as via the use of the Global Positioning System (GPS) or other positioning system using wireless radio signals.

Many of the methods described in this invention include steps involving the Communications sub-system. The steps typically include transmitting digital data to a remote computer or communications device, and receiving results digitally. In some cases, the steps include communications with or via another portable device such as a handheld computer or cellular telephone. In such cases, signals from the device described by this invention are communicated to a portable device including but not limited to a cellular telephone or handheld computer. The second device then either processes data internally and transmits results back to the first device, or the second device relays information to a remote system using its own communications means. In this case, the second device acts as a communications bridge between the device and a remote system. It is to be understood that these steps, or variations thereof, are steps involved in communications between the device and remote systems.

Output/Display Sub-System 105:

The Output/Display sub-system 105 provides information output capability to the invention. Any one of a number of methods can be used, singly or in combination. The system includes one of the following:

(a) Loudspeaker 150 to provide audio information output.

(b) Headset or earphones 151 to provide audio information output.

(c) Miniature virtual display device 152, which provides high-density information display by placing the eye close to the display screen and viewing a virtual image.

(d) Small display screen 153, provides information, and/or a user interface.

The data that is to be displayed may be from a variety of sources, including text and graphics data. The data format may take any form, including HTML and derivatives thereof.

In one embodiment, the audio output means is shared by the auscultation function and other functions. This is a unique aspect of the invention, since listening to a stethoscope is a common practice in the medical work environment, and the invention provides for listening to numerous other audio and information sources via the same means, making audio a natural means of information communications in the medical environment. The information output is also private, allowing workers to listen without patients overhearing.

Functional Description

The invention is used by medical workers to make physiological patient measurements, access data, store information, access information, make medical diagnoses and/or communicate with computers and people. It is the purpose of the invention to provide portable digital functions to medical workers, in order that they may take advantage of advances in numerous digital technologies as an integral part of their workflow. Such digital technologies includes measurement, information, and communications functionality. The purpose of these functions is to make information and communications an integral part of the work flow of medical workers, by uniquely combining the elements of the invention in a portable form, and using user-friendly, timesaving methods to access data and information. This promises to change the way that medical workers use information, making information an integral part of medical practice, available quickly and easily when needed. The flow of information includes facilitating the transfer of information to the patient as well, since the methods described by the invention provide for the transmissions of digital information to the patient.

Specifically, the invention uses one or more of the following technologies:

(a) Speech recognition and voice recognition.

(b) High-density low-power memory.

(c) Wireless analog or digital communications.

(d) Text-to-speech and data-to-speech technology.

(e) Low-power electronics using a portable power source.

(f) Wide area digital communications technology, such as the Internet and POTS.

While the invention may be built without stethoscope or medical measurement functionality, the preferred embodiment of the device includes an electronic stethoscope or other physiological measurement means, combined with one or more of the following functions:

(a) Pager.

(b) Cell phone.

(c) Wired and/or Wireless Communication to transmit requests for data and receive data from a database.

(d) Built in database of auscultation sounds, patient data, medical information, and/or pharmaceutical information.

(e) Heart Rate Monitor.

(f) Blood Oximetry monitor.

(g) Korotkoff signal processor to assist with blood pressure measurements (h) Blood Pressure Monitor (i) Thermometer (j) Speech recognition (SR) and/or voice recognition (VR) system (k) Speech generation text-to-speech or data-to-speech system (l) Database search engine (m) Internet protocol communications (n) Internet interface for performing internet searches (o) Automated diagnostic software to perform signal and data analysis and guide medical diagnostics (p) Natural Language Processing (NLP) to convert spoken input into command, control and search functions (q) Video input and output means, to input, record, playback and display static/still and dynamic/moving images.

The above list is not an exhaustive list of all technologies and functions. Specific functions, methods and applications are described below.

Various methods are described as part of the invention, for manipulating signals, measurements, data and information.

One method relates to access of medical information. The medical information includes, but is not limited to, drug dosage information, drug interaction data, patient records, medical research information, medical protocol and treatment information, medical insurance information, patient history, billing information, medical procedures, and other information related to the treatment of patients. The method of working with this information includes the following steps: The user enters commands or requests via the User Input sub-system, using the means provided. Such means include keystrokes, touchscreen, rotary dial, or speech input. The Electronic Processing sub-system processes the commands, and searches the data stored in the Digital memory. The results are then formatted and output via the Output sub-system. In one embodiment, the input means is speech via the microphone, and the output means is audio, using text-to-speech means. The audio output means may optionally be the same means as used for auscultation sound output in an embodiment that includes auscultation means. In another embodiment, the output means is the virtual display device, meaning a small screen, viewed at close proximity to the eye, to provide an image to the viewer that is perceived to be larger than the actual screen itself. These output means are not mutually exclusive. The virtual screen may provide either monocular or binocular viewing means.

A second method uses the Communications sub-system and a remote data source. The method is as follows: The user enters commands or requests via the User Input sub-system, using the means provided. Such means include keystrokes, touchscreen, rotary dial, or speech input. The Electronic Processing sub-system processes the commands, and transmits the request to a remote computer system containing the requested data and information. The remote system performs the steps of searching for appropriate data. The results are then formatted, transmitted back to the device, and output via the Output sub-system. In one embodiment, the input means is speech via the microphone, and the output means is audio, using text-to-speech means. In another embodiment, the output means is the virtual display device.

It is to be understood that alternatives which are covered by the invention include performing some of the steps within the remote system, such as speech processing and text-to-speech conversion. Variations of the method and structure described above can achieve the same result, and the above descriptions should not be construed as limitations on the structure and method of the invention, or of the type of data for which the invention is useful. For example, the speech recognition functions, or the text-to-speech functions can be performed by a remote system, decreasing the processing burden on the portable device carried by the user. Such a method still achieves the result of being able to enter speech commands for searching medical information systems, and receiving speech output. A second variation of the method includes the use of a second portable communications device which is used as an intermediary communications means between the first device and a remote system. For example, the first portable device might communicate with a cellphone or handheld computer, which in turn might contain the requisite information, or might in turn communicate with a remote system, acting as a bridge between said first device and remote database system. This method has the advantage that the first medical device uses the wireless communications or storage capability of a more general-purpose computing or communications device such as a handheld computer or cellphone.

A further method included in the invention is the storage of information related to a patient and/or user either locally in digital memory in the portable device, or in the remote system. As an example of such a method, the following steps would be performed: The user enters information via the User Input sub-system. The input is then converted to a form suitable for storage in a database. The data is then stored locally in digital memory, or transmitted via the Communications sub-system to a remote database or handheld computer for storage. The data stored may include, but is not limited to, patient name and identification data, examination results, drug dosage, tests ordered, tests results, physiological measurements, procedures and services rendered, billing information, and time and duration of service. If the data is stored locally in digital memory, the method includes the step of later transferring the data to a computer system for inclusion in a patient's medical and billing records. An intermediate communications means may also be used, such as a cellphone, telephone or handheld computer, which bridges data communications between the device and a remote computer system. The unique aspects of this method are the combination of speech recognition, combined with wireless communications and the medical data as described. The method includes software for formatting the data into an appropriate database record or document from the speech input, when speech input is used. The automation method includes the steps of identifying keywords or identification phrases which the formatting software uses to allocate information to categories such as tests ordered, test results, measurements, physical findings, times and dates, and other relevant data. This allows the speaker to use a natural language input format, with some limited structure, and using software processing to partition the data types, and compile a report with a more uniform structure. The method also simply allows standard transcription. In this case, the uniqueness of the invention is the embedding of speech recognition into the process, and in a preferred embodiment, into a portable device.

With regard to the recording of patient record information, it is to be understood that patient records may be transmitted both from and to the device. Therefore, the user may make a request for a patient record, and have a remote computer system transmit the patient record to the unit for review and updating. Such record may include audio recordings, images, test results, and other data specific to the patient.

As a variation of this function, the invention includes a voice recording method, as follows: The user dictates into microphone 130, the sound is stored digitally, either in raw or compressed form, and the stored recording is then transferred via the Communications sub-system to a speech recognition system located on a remote computer. Alternatively, the speech recognition function is built into the invention, and the converted text information is stored and later transferred to a remote computer for storage and/or printing. The recorded data record might also include physical or physiological measurement data, and other automatically or manually generated data such as time and date. The inclusion of this function in an information or measurement appliance obviates the need for a separate dictation or patient reporting device or service. The computing device that ultimately stores the patient records or transcribes the recording from speech to text may be located remotely and accessed via cable, telephone, internet, or wireless link. For example, data from the unit in the form of voice files or data files may be transmitted or emailed from the invention to the remote system, or transferred via a cable or infrared link. The uniqueness of the invention with regard to dictated data lies in the combination of measurement means used by the medical worker with voice recording means. A further aspect of uniqueness of the preferred embodiment is the dual use of the stethoscope audio output means—the audio output means for playback and feedback of voice recordings may be the same audio output means as that used for auscultation, or it may be a separate audio output means. The combination of voice recording means and auscultation means has not previously been reported, and is a unique aspect of the invention. The benefit lies in the fact that dictation means is no longer necessary as a discrete and separate device from the auscultation device.

While the preferred embodiment of the voice recording system provides for speech recognition functions either within the device or remotely, it is to be understood that the voice recordings may also be transferred digitally to a remote device, and manually transcribed to text by a person listening and typing the dictated text. In this case, the fundamental benefit of the device is that the voice recording means is combined with the auscultation means such that a common power source may be used, and audio components common to voice and auscultation may be used, to lower cost, size and weight of the invention. For example, the audio output means used for auscultation may be the same means used to listen to recorded voice for review or playback.

In the preferred embodiment, the speech output is provided via the same audio output means as that used for auscultation. If a visual display means is used, a miniature display of less than 4 inches diagonal measurement is used, or a virtual display device is used. In the preferred embodiment, the device has the form of an electronic stethoscope, with headphones or earphones and auscultation sensor. The preferred embodiment also includes the communications means, which uses wireless radio communications means. The preferred embodiment as described does not restrict the invention, since other means may be used to perform the same methods of data access.

One important aspect of the invention and the methods associated therewith, is the validation of access to patient records and medical information. Specifically, patient privacy is becoming an important problem, as access to patient data becomes easier. The invention includes a method for identifying the personnel requesting information using voice as an identification means, recording the request for such information, and validating the authorization for such a request. The method includes the following steps: The user (requester) enters a voice or speech command or identifying voice signal. The voice signal is used, either raw or preprocessed, to identify the user. This identification step may be done locally from local storage, or the identification data (voice or voice parameters) may be sent via a communications link to a remote system which contains voice verification or identification database information. The identity of the user is then performed, and the request logged for future reference. If a limited number of authorized users may gain access to the patient data, as an additional step, the voice identity of the user is compared to the authorized list, and approval is either granted or denied. If granted, the requested patient information is transmitted to the device via the communications channel, or the information is simply transmitted without authorization if no authorization is required. At a later time, the identity of the requesting person can be checked for each patient. This process allows medical workers to access patient data in realtime, but ensures that requesters are identified so that fraudulent or unauthorized access can be verified and prosecuted. The same identification means may also be applied to the storage of new information is a patient record, in order to control and audit the authority to modify patient records. This means of identification can be extended to include telephone or computer access, for situations not requiring portable access.

The voice verification method is also applicable as an anti-theft method for the portable device. The steps are as follows: The voice identity of the user is compared to the an internal voice identification record in digital memory, the identity record of which has previously been stored. If the identity matches, the device continues to operate. If not, the device either ceases to operate, or operates with some limitations, such as time limit or a limited number of functions. This voice verification method may be applied to a wide variety of portable devices which are subject to removal or theft.

The use of speech or audio output offers broad applicability. The invention includes the capability to make physical or physiological measurements using the Sensors sub-system. The measurements include, but are not limited to auscultation sounds, temperature, blood oximetry level, blood pressure, blood glucose level, and other physiological and physical measurements. The invention includes means for converting such physical measurements to medically useful data, such as numerical results. The numerical or physiological results can then be converted to speech output to be sent to the user via the audio output means. This has the advantage of giving the medical worker patient measurement and test results aurally. An alternative, of use in a portable device, is to display the information on a miniature or virtual display of less than 4 inches diagonal measurement. In the preferred embodiment, physiological measurement results are provided in speech form via the same audio output means as that used for auscultation.

The ability to store and transmit patient history and medical information from the device to remote medical diagnostic computer systems facilitates further information processing capability of value to the medical worker. The invention provides for the remote system to perform automated diagnostic analysis, provide suggested or standard treatment, and diagnostic or research information. The method also allows for the inclusion of solicited or unsolicited voice or display messages to be included in a return transmission to the user, such as drug or medical product information. The method is as follows: Patient condition information or disease information, or a discrete information request is transmitted from the device to a remote computer system via a wired or wireless digital communications link. The patient record or disease information is then analyzed by a software search system which matches potentially useful products, medical research or treatment information with the patient's condition, medical record, or information request. The remote system then optionally combines medical information to be sent back to the user with product information, and the combined message is transmitted and displayed or played back aurally to the user. An alternative reply method is to perform the matching function as described, and then email or otherwise transmit relevant product and medical research and information to an email address or data reception site associated with the user, and known to the remote computer system. The user then receives email or data which includes product information, medical research, or other useful information related to the patient's condition or disease in question. The email or data response may take the form of a discrete transmission to an email account, or simply a search result stored in a computer system accessible by the requester, such information being formatted and presented to the requester when communicating with said computer system, such as logging into the Internet and viewing Web customized pages or links. The user or medical practitioner benefits by receiving medical information without having to manually perform research tasks. The method of the invention can be extended by further transmitting digital data, email or a report to a computer or data site accessible to the patient, the data response having been compiled as a result of a request entered by the medical worker into the portable device described by this invention. In this case, the patient benefits by receiving medical information and advice directly, as a benefit of the medical exam. Information therefore becomes integral to the practice of medicine, providing the practitioner with real-time or delayed information distilled to be directly relevant to a given case, and the patient benefits by receiving additional information that can help to educate the patient. In the case of using patient medical records to derive search requests, the method provides for stripping patient-specific information from the search request, in order to maintain confidentiality.

A further application of the invention is for telemedical diagnostic services. The method is as follows: The user makes a physiological measurement such as auscultation, glucose or blood oxygen measurement. The measurement, and optionally voice or system identification information is transmitted via communications means to a central medical screening center staffed by qualified medical practitioners or nurses. The communications means in this case might be of a consumer nature, including but not limited to wired telephone, cellphone, or Internet access. Once received at the remote medical center, the medical measurements and data are analyzed by said medical practitioners or nurses (analysts). The analyst then communicates with the user, who may be a patient or caregiver, and recommends a course of treatment or action resulting from the measurement analysis, and additional information. The return communication may via telephone or email or other data transmission means. The invention provides for the measurement and communications functions to be combined. If voice communications with the medical analyst is included in the method, the microphone and audio output means used for the communications on the user end may optionally be integrated into the portable device described by this invention, and use the same audio output means for auscultation, measurements and voice communications. This allows the user, patient or caregiver to listen to auscultation sounds and have a telephone conversation concurrently or sequentially. The communications between the device and the remote analyst includes data for identification and control commands to allow the analyst to control the device operation and read results directly. The communications may optionally include video connection to allow the analyst to view the patient while performing measurements.

While the telemedical method is preferably performed in real time, a method which uses email or delayed data transmission is also part of this invention. Using this method, the measurements, voice and data are emailed or transmitted via the Internet or other data communications service to a remote site, where an analyst evaluates the information and responds via data communications means or telephone. The analysis may also be performed automatically by signal processing and computer analysis means. An important aspect of the invention thus used, is the ability for the remote system to use identification means to store data and measurements in a patient database, and use sequential communications records to analyze the progress of the patient from one communications to the next. This is especially valuable for an asthma or pulmonary condition, whereby sequential records may be listened to by the analyst, for baseline and comparison purposes.

The invention may optionally include local measurement or analysis capability. The steps in the method would thus include the following: Physiological measurements are made, the signals are analyzed within the portable device using signal processing and data processing means, and a recommended course of action is displayed or output via the audio output means. The recommended courses of action include, but are not limited to—no action, monitor situation, call medical center. In this case, the diagnostic algorithms are included in the Digital memory of the device.

The invention also includes capability to store reference auscultation sounds in Digital Memory. There are two purposes for these reference signals. In one method, the user can listen to reference sounds in order to make a manual comparison of a patient's sounds with references in order to manually determine similarity. In a second method, the reference sounds are used by built in analysis software to compare a patient recording with the reference sounds, in order to perform a matching function to find the most similar sound, and render a potential diagnosis.

The telemedicine applications of the invention are enhanced by the combined functions described in the invention. Specifically, the combination of stethoscope, oximetry, glucose and/or voice functions, combined with the communications sub-system, allows for measurements and annotated information to be transferred via telephone or data transmission to a central diagnostic center, along with patient identification data, for remote evaluation. By including a microphone and audio mixing in the device, the analyst at the remote site can communicate with the patient or caregiver.

A further example of the use of the invention is for communicating with a medical worker. By including a built in pager device, physical locator device or cellular telephone, the medical worker has communications functionality built into a medical information or measurement appliance, obviating the need to carry a separate communications device. The communications functions can be performed via the same audio means as those used for other audio input and output functions.

The communications means provided in the device may be of a general-purpose nature, such as pager or cellphone. While during working hours, the worker might find the combination of medical measurement functions, and specifically auscultation, with communications functions to be useful, one embodiment of the device allows for the communications functions to be physically separated or disconnected from the communications functions. the worker can therefore carry the communications functions in a compact manner without having to carry all components of the invention all the time. In such an embodiment, the medical measurement or output means, such as auscultation sensor, oximetry sensor, or earphones, may be mechanically decoupled from the main body of the device to produce a more compact device.

The productivity enhancement of the invention are enhanced by including various additional Internet and database functions which are easily activated by the user. One such example is a request for a database or internet search related to a patient's history or physiological measurements. The patient's records, or the user's inputs via voice or keypad, are converted into an Internet or database search, and the results provided back to the device, or sent to another destination, such as the user's email address. This service might include transmission of the physiological or patient information to a diagnostic database for automated diagnosis or peer review. The invention provides these functions by providing a connection between the point of care and other computing resources via its communications sub-system, either in real time or via a stored and delayed transmission.

The recordkeeping functions are enhanced by various automated annotations. These include time, date, personnel on duty, and/or drug and other information entered via voice or barcode. The information may be transferred to a billing and management system, as well as a patient information database. This is an example of how information and data are seamlessly integrated into the patient care process—a central purpose of the invention.

One of the problems encountered in medical education is that of examining medical students and nurses on their auscultation skills. The invention provides a means to administer testing of such skills, using the following method: An electronic stethoscope with auscultation means is operatively connected to a personal computer, or remote computer system via a digital communications means. The computer contains a digital memory with various heart, lung and other body sounds, which are transmitted via the communications means to the stethoscope, allowing the student to listen. Included with the auscultation sounds, is a voice message stating a multiple-choice question. The student then listens to the sound, and is provided with a means, either on the stethoscope or on a connected device such as a personal computer, to enter a selected answer, which is then transmitted to the remote computer system for grading. The system optionally has a voice recognition identification means to validate the identity of the student taking the test.

This educational method can also be applied to a learning environment. In this situation, the invention consists of an electronic stethoscope, combined with a database of recorded heart, lung and other body sounds, recorded on a digital medium such as, but not limited to, compact disk, floppy disk, or digital memory. Alternatively, the sounds may be transmitted via a communications medium such as the Internet. The invention then provides a means to connect the stethoscope operatively to facilitate the playback of the sounds via the stethoscope's audio output means. Additional controls are provided to allow the listener to replay, skip, or otherwise control the playback of these sounds. The uniqueness of the invention lies in the facility to reproduce the recorded sounds through the same audio means as is used by the practitioner to listen to perform auscultation, rather than using a headphone set connected to an audio system. This ability makes the stethoscope into a teaching tool. The transmission of the sounds digitally to the stethoscope is also unique, and is an improvement over previous methods in that sound quality is maintained. The listener is therefore listening to digitally transmitted auscultation sounds through a stethoscope, rather than using a general-purpose audio system. By using the Internet or other wide area network system to perform these tasks, distance learning and teaching is facilitated, which has not been reported before.

All of these combinations are unique in that they combine medical management functions into a wearable device. Previous inventions might provide some of these functions, but do not possess the convenience of combined functions, which allows a more integrated functionality, ease-of-use and integration of patient measurements and database information.

Figure 2:
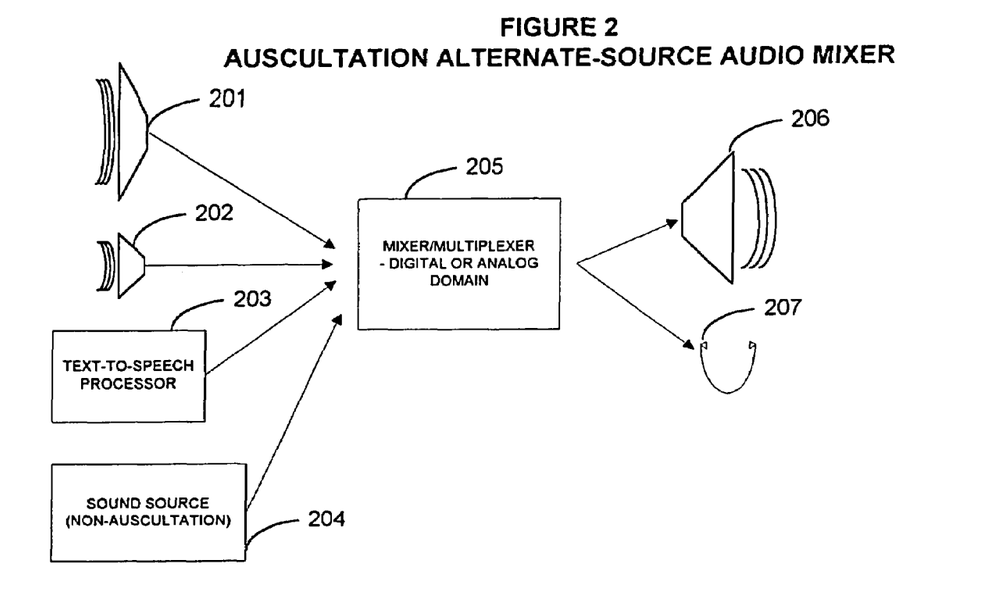
FIG. 2 is a block diagram showing the audio mixing of auscultation sounds and alternate audio sources.

One of the unique aspects of the invention, is the combination of audio sources for information and measurement output. FIG. 2 shows a functional diagram of one embodiment of the invention, whereby the auscultation sounds and measurement and information sources are mixed and reproduced via the same audio output mechanism. Auscultation sounds from sensor 201 are processed. The microphone 202 provides an input source that can be mixed with the auscultation signal. Information data from the text-to-speech (data-to-speech) processor 203 is also accessed or generated, and converted to speech. Any other sound source with no auscultation content 204 is also available to the mixer. It is then mixed or multiplexed by mixer/multiplexer 205, in order to reproduce it through the same audio output means—speaker 206 or headphones 207. In the preferred embodiment, measurements such as heart rate or time intervals are computed and converted to speech to be played through the same headset used for auscultation. The preferred embodiment includes the stethoscope sensor, and a data-related voice source, such as text-to-speech processor 203 or recorded sound segments from a stored source, such as 204. The mixing function also allows for the mixing or multiplexing of ambient sound with auscultation sound. This may be automated, whereby the sound source is switched to auscultation when the system senses that the auscultation sensor is in use. Such sensing can be done by measuring the signal amplitude and/or signal frequency content from the auscultation sensor. When the amplitude increases, or the subsonic frequency content increases, the system switches to auscultation sensing. The mixer is thus intelligent, and is able to determine the source of the sound to be presented to the output means.

The digital rotary switch provides an easy-to-use user interface. As the knob is rotated, the display or voice output indicate modes and/or menu selections to the user. Once the user gets to the desired option, the rotary switch is pushed to "click" (select) the option.

The output devices 152 and 153 also provides a unique method of displaying information on a small medical device. The virtual display 152 allows images to appear larger than they actually are, allowing large images to be viewed on a small device. In one preferred embodiment, the device includes a stethoscope sensor, and a virtual display device. Alternatively, the display device may be a small display 153, possibly, but not limited to being less than 4 inches diagonally, which displays data, images and the user interface.

Another output means is the conversion of digital information to audio/speech output. This is done in the Electronics Processing sub-system, and allows digitally-stored information to be output via an audio means such as speaker or headphones. Information might include heart rates that are measured from the auscultation waveform, or intervals between events within a heart cycle. In the preferred embodiment, the measurements are performed automatically i.e. by a software function. An alternative is that the waveform is reproduced, and the user pushes a button at the time of each event being measured. The electronics processor then finds the nearest events to the button push times, and produces a measurement, provided in voice format via the audio output device.

The digital memory 121 is used to store programs, data, voice recordings and other data required for correct operation and features. A sub-section of this memory may be placed on a removable medium, providing an alternative method of data exchange. The memory means may be any digital storage medium, and may be partitioned physically and logically into RAM, ROM, NVRAM, program memory, data memory, audio memory, or other partition that provides for an efficient design.

Some of the benefits of the invention lie in the combination of core functional units or sub-systems, which can be shared by various functions. Therefore, the battery pack can be used as a power source for communications, measurement and computing functions. This is unlike the separate device situation, whereby each device has its own power source. A similar benefit is derived from using a central processing unit to manage all measurement, input, output and communications functions through various software modules. This provides a potential for cost saving over physically separating these functions.

The combination of functions made possible by this invention provide a unified, convenient platform for functions and features useful in the medical environment, whose unification adds significantly to the convenience and ease-of-use of these functions compared to a situation where each is offered separately.

While the invention has been described in the medical work environment, the same elements may be combined to form a wearable information, measurement and communications device for other applications. These other applications do not materially change the combination of elements in the invention, but do change the content of the information. Other examples include legal information and databases, law enforcement and security situations, inventory management, whereby the information relates to products and materials in a warehouse, and other situations where communications, measurement, input, and output are combined in a unique manner.

While the invention describes various potential combinations of elements and methods, and is intended to cover a broad range of options, it is important to specifically describe some preferred combinations of elements. While this brief list includes specific combinations, it is to be understood that other combinations are covered by this invention. The term "stethoscope" shall include devices that use ultrasonic signals to produce audio representation of body functions:

(a) A device comprising a stethoscope combined with a pager means.

(b) A device comprising a stethoscope combined with a cellular telephone.

(c) A device comprising a stethoscope combined with a voice recording means.

(d) A device comprising a stethoscope combined with a wireless communications means using spread spectrum digital communications.

(e) A device comprising a stethoscope combined with wireless communications means using 900 MHz digital communications.

(f) A device comprising a stethoscope and oximetry measurement means. Such combination may be housed within the same housing, as a combined portable instrument with portable power source, such power source potentially being separate or shared by both stethoscope and oximeter.

(g) A device comprising physical and physiological measurements means, with speech output of measurement results.

(h) A device comprising physical and physiological measurement means, with speech output of measurement results, and means for modifying the language used for output.

(i) A device comprising physiological measurement means combined with speech recognition means.

(j) A device comprising physiological measurement means for auscultation, combined with speech recognition means.

(k) A device comprising a medical database containing pharmaceutical information including but not limited to combined effects of various drugs, and drug dosage requirements based on patient physical characteristics, such database being combined in said device with speech recognition means to access said database using speech input.

(l) A device comprising a medical database as defined in (k), whereby the database output means is via audio output, in one or more languages.

(m) A device comprising a medical database as defined in (k), whereby the database output means is via a miniature virtual display placed close to the eye which generates a virtual image.

(n) A device comprising speech recognition means, digital memory means, and software to interpret a (primarily) medical vocabulary, whereby speech recognition means is combined with software to generate structured patient medical records database information from freeform unstructured speech input. This is commonly referred to as Natural Language Processing (NLP).

(o) A device as described in (n) whereby speech recognition means is used to access patient medical records from a remote system via a wireless digital communications means.

(p) A device comprising physiological measurement means, combined with voice recognition means, whereby voice recognition means determines the level of device functionality. This is used for securing the device.

(q) A device as described in (o) combined with voice recognition means, local or remote, whereby voice recognition is used to determine access to patient records.

(r) A device comprising electronic stethoscope combined with medical information database, whereby medical information is searched via speech recognition means, and medical information results are output via an audio output means, said audio output means being the same audio output means used for auscultation sounds.

(s) A device comprising a stethoscope combined with a miniature virtual display device, said display producing a virtual image when placed close to the eye.

(t) A device comprising a portable communications device with spread spectrum digital communications means and miniature virtual display device.

(u) A device as described in (r) connected via said spread spectrum communications means to a remote medical database system, said database system including medical research information or patient records.

(v) A device comprising a stethoscope, communications means, and control means operating via said communications means, whereby a remote user can control stethoscope operations and listen to auscultation sounds.

(w) A device as described in (v) whereby communications means carries voice and auscultation signals simultaneously or alternately.

(x) A device comprising a stethoscope with additional microphone and multiplexing and mixing means to multiplex or mix sounds from auscultation source and microphone, whereby sound source is determined by auscultation source signal amplitude and low frequency characteristics.

(y) A device as described in (v) whereby remote database system includes software to search medical database and generate medical research or product information reports based on patient medical record contents.

(z) A device as described in (y) whereby patient identity is removed from search request submitted to database, in order to protect patient privacy.

(aa) A stethoscope with voice recording means, whereby voice recordings are transferred via a digital communications means to a personal computer.

(bb) A stethoscope with voice recording means, whereby voice recording are transferred to a personal computer or remote computer via digital communications means, said computer containing speech recognition means to convert said voice recordings to text-based reports and information records.

(cc) A stethoscope with digital memory means, said memory containing auscultation sound recordings for various medical conditions, combined with audio output means to listen to reference auscultation sounds, and recorded auscultation sounds, for the purposes of comparing patient sound to known one or more recordings, in order to assist listener in making a diagnosis.

(dd) A stethoscope as in (cc) combined with pattern recognition means, such that patient sounds is compared to reference sounds, and suggested matched sounds and diagnoses are presented to the listener via auscultation audio output means.

(ee) A stethoscope combined with infrared digital communications means, said communications means being used for transmission of auscultation sounds and digital voice recordings.

(ff) A portable wireless communications device with facility to connect physiological sensing and output means using the same power source, said connection being mechanically designed such that the communications means can be mechanically separated and operated independently from the physiological sensing components.

(gg) A software program whereby patient records are scanned for disease and treatment-related keywords, and patient-specific identification data are removed; said resulting disease and treatment information being applied to a search request for medical and product information; said medical and product information being transmitted via a communications means to said patient, or patient's caregiver or physician.

(hh) A portable video recording means combined with a wireless communications means, said wireless communications means having capability to transmit video images to a patient record database stored on a remote system operatively connected to said video recording system. By video, is meant a means for capturing both still and moving images.

(ii) A stethoscope with wireless communications means and Internet protocol software to send and receive email and web page data over the Internet.

Physical Embodiment

Figure 3:
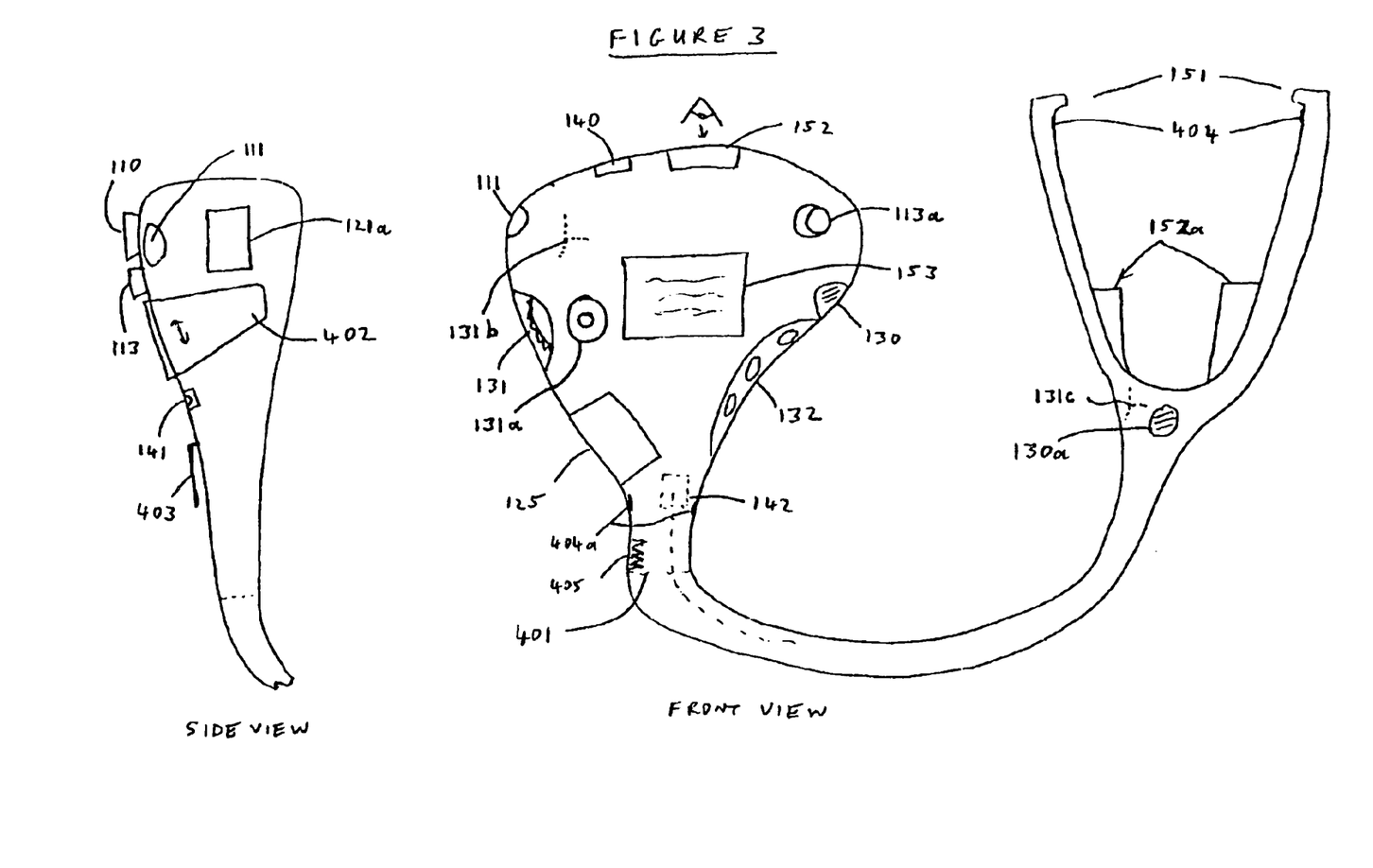
FIG. 3 shows one physical embodiment of the device with integration of multiple functions housed in a single device.

FIG. 3 shows one physical embodiment of the device, to illustrate the integration of functions into a single unit. This is a preferred embodiment, but is only one way that the invention may be physically packaged. The main body shown in FIG. 3 may also take the form of a general purpose handheld computer with medical sensors physically attached or cabled to the handheld computer to provide the same functionality as shown in FIG. 1. In this embodiment, most of the electronic processing 102, user input 103, and output/display functions 105 would be provided by the handheld computer's built in functions.

The device consists of an enclosure with elements of the design. Input from the user is performed via keypad 132, rotary dial 131 and/or microphone 130. The microphone may optionally be placed on the headset shown by microphone 130a, which has the benefit of proximity to the user's mouth for speech input.

As an alternative or adjunct to input means 131 are shown a joystick 131a and an internal motion sensor 131b, or 131c placed in the headset. The joystick is used to provide 2-dimensional input, with a possible pushbutton for affirmative selection of a control option. The motion sensor provides 3-dimensional and rotational sensing to allow the user to control the device by moving the main housing through space in specific directions. Similar actions can be done using head movements, using the headset-mounted 131c.

Output of information is provided via a number of potential means, including display 153, virtual display 152 or 152a, and/or headphones 151. Placing the virtual display on the headset as shown in 152a has the benefit of providing binocular vision. The headset may be disconnected via connector point 401.

Communications is effected via connector 141, Infrared communications port 140, and/or wireless communications means and antenna 142. The antenna may optionally be extended into the headset cable assembly.

The digital memory 121a means may optionally be removable and accessible from the outside of the enclosure, as shown.

Sensor means are provided by stethoscope or auscultation sensor 110, oximetry sensor 111, or other sensor 113 and 113a, which may be a barcode scanner, image sensor, video/camera input lens and imaging sensor, or other sensing means, such as ultrasonic probe. An ultrasonic probe may be used as the means for doing auscultation or blood flow measurements, in place of the more conventional acoustic sensor. By stethoscope, is thus meant any such means for performing auscultation. Ultrasound may also be used in this invention for imaging, such as for echocardiography or obstetrics, using the display means for viewing images. The various sensor means may be detachable or removable, such that they become accessories to be added to the basic housing. In such a case, the housing is designed such that there are cavities for inserting the various sensor and measurement means. The image sensor means allows for the inclusion or attachment of close-up lenses or ear-tip probes, in order to view eardrums, nostrils, throat, or take close-up images of skin or other body parts, for the purposes of recording in medical records.

Sensor 113a is shown to have an orifice through the housing. This allows for sensors which measure breath, or optical transmission characteristics. In the case of breath, either lung capacity or breath chemistry may be measured by the patient breathing through a tube attached to the main housing. In the case of an optical measurement, the patient might insert s finger into the orifice, which may in this case be closed at one end. Sensor 111 may operate in a similar manner. In all cases, the invention allows for the inclusion of disposable sensors and/or covers to ensure sterility. Sensor 11 may also be a reflective optical sensor. An alternative means of connecting additional sensors to the device include using electrical cabling, connected to durable or disposable sensors.

Convenient physical enclosure features are provided by a belt clip 403, which has previously not been associated with a stethoscope, and a movable cover 402 to protect the medical or other sensing means. Power is provided by energy source 125, which may be a battery or other electrical energy source. Contacts 404 or 404a are located on the surface of the enclosure, and provide a means for clipping the device to a charger, suspended by the earpiece or held around the case, to provide charging while not being used. Alternatively, an inductive/magnetic connection may be used via coil 405 placed inside the device, which can provide inductive connection to an external charging circuit. This coil may also be used as a communications means, using higher frequencies to transmit data, while lower frequencies are used for power transfer. The entire housing may be sealed to allow for sterilization, or disposable covers may be attached to protect the device itself from touching patients.

Figure 4:
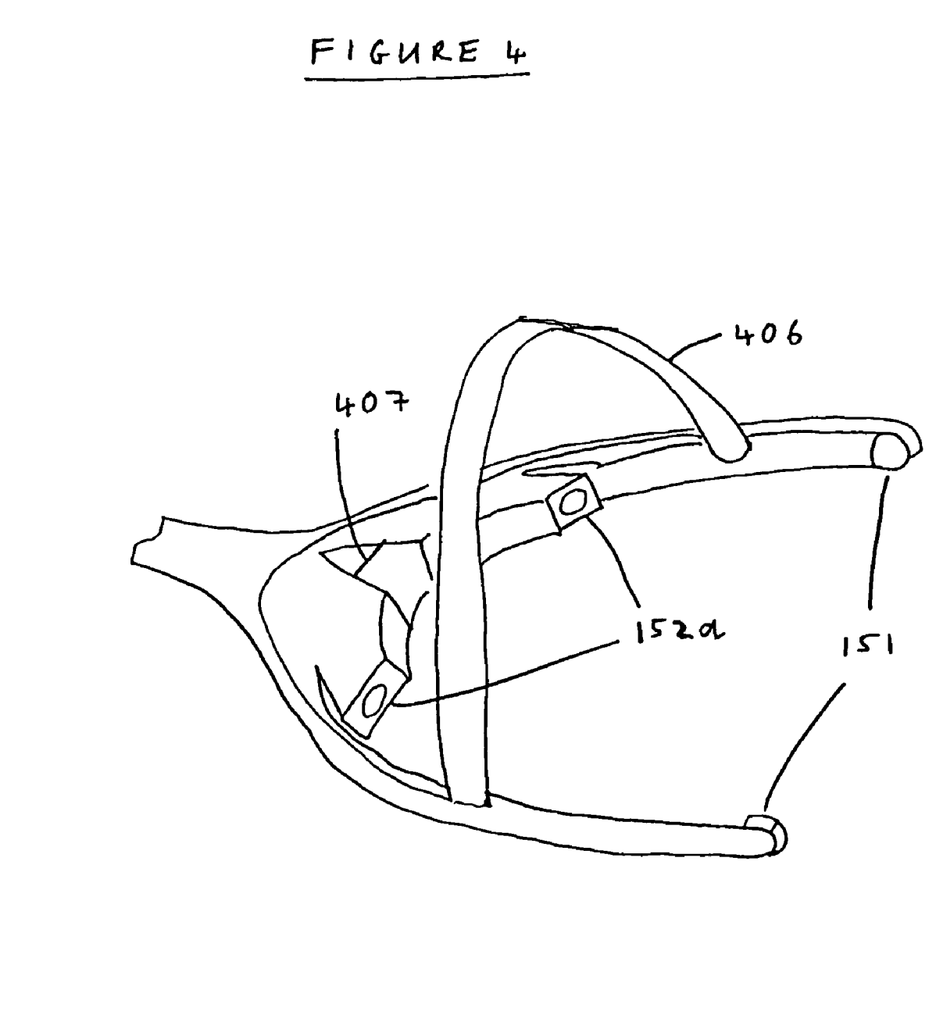
FIG. 4 shows a binocular virtual display means built into the stethoscope headphone assembly.

FIG. 4 shows further detail of a preferred embodiment of a binocular virtual display means, built in to the stethoscope headphone assembly. A headband 406 is attached to the headphone assembly, such that it can be moved from a position planar to the headset (out of the way, potentially fitting into a slot), to a position at approximately right angles to the headset such that it becomes a support that fits over the top of the viewer's head aligning the eyepieces of the display 152a to the viewer's eyes, and holding the headset/display in position. The headband 406 may be of a solid material, or a flexible substance that adapts to the shape of the viewer's head. FIG. 4 also shows an eyepiece distance adjustment 407, to allow the distance between the eyepieces of a binocular display to be adjusted to the viewer's preference. This distance is adjustable such that it is somewhat independent of the distance between the earpieces 151. The eyepieces 152a allow for dioptric adjustment or insertion of prescription lenses, to further customize viewing quality to the needs of the viewer. Such accommodation is also provided for in a monocular eyepiece 152. Any convenient means for attaching or positioning the display may be used, for example, using a support which rests on the viewer's nose.

Figure 5:
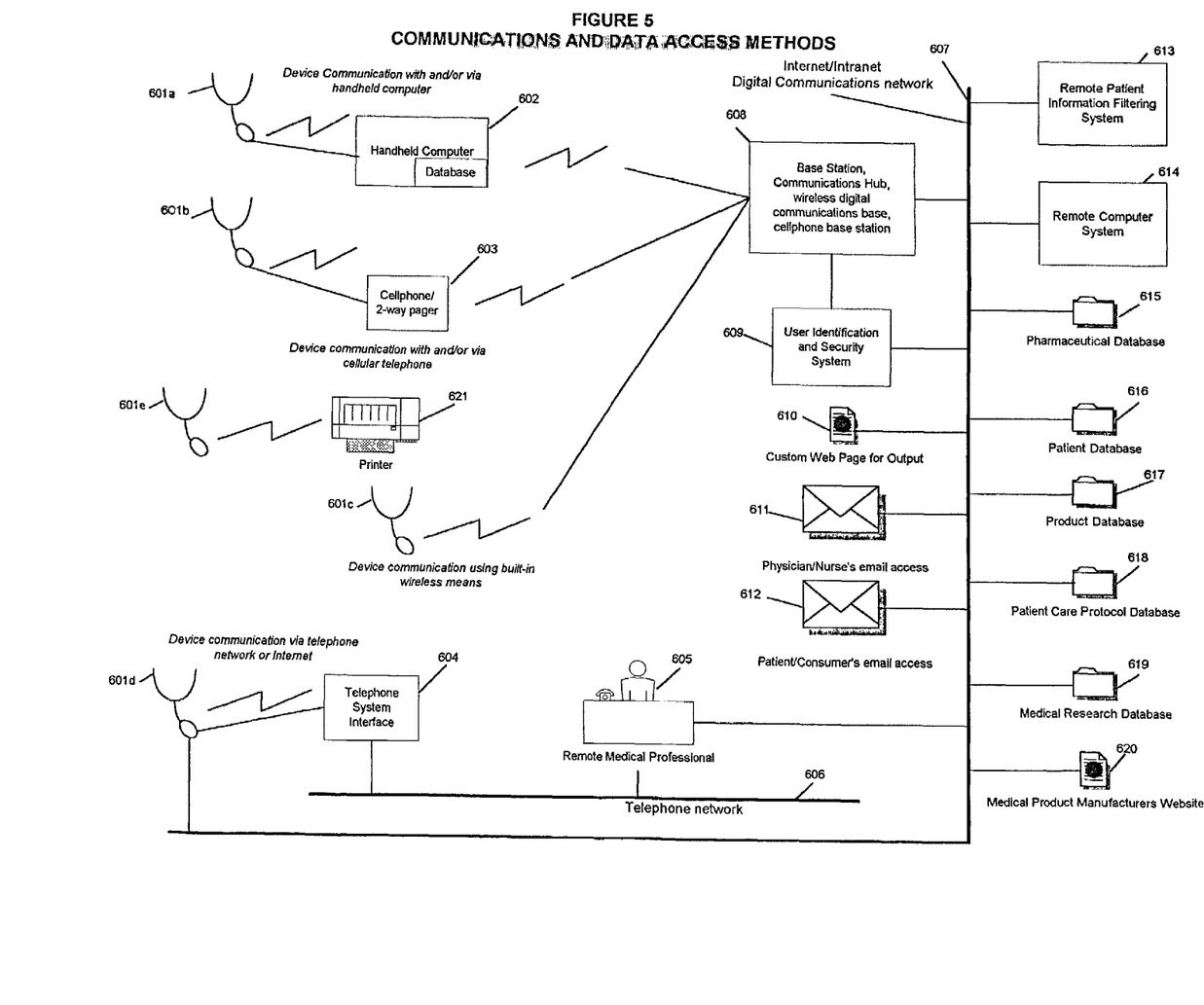
FIG. 5 shows communications and data access methods and functions.

FIG. 5 shows the functional aspects of many of the methods in this invention. The device is shown as 601a-e. In one embodiment, the device 601a communicates with a handheld computer 602 with built in database. The database might include many forms of data, as discussed elsewhere in this description. The device communicates with the computer 602 via a wireless or wired connection. In turn, the computer 602 may have wireless communications capability to access further computer or information networks 607, acting as a bridge to the device 601a. Alternatively, the device 601b communicates via a wired or wireless connection to a cellphone or 2-way pager 603 which in turn communicates with a data network 607. Finally, the device 601c may have a built in communications means which directly communicates with a data network 607. Also shown is the ability of the device 601e to communicate via a wireless link to a printer 621. The device 601d may also communicate via the telephone network 606, either directly or via an interface device 604.

The purpose of the communications methods and means, is to access a telephone or data network. The devices 601 communicate either directly or via a Base Station 608 to a data network, Intranet, or Internet 607. The Base Station 608 may include, or be linked to, a security and identification system 609, which may include encryption of data, voice identity verification and audit trailing of accesses, and other security means, to protect access to patient records and other information and services.

Many of the purposes and methods associated with the invention and associated methods include communication with, and use of various data, information and knowledge bases, available locally on an Intranet or via the Internet or other data network. FIG. 5 shows some of these methods and elements, as examples. Data requests from devices 601 may be transmitted to a remote computer system 614, which accesses such databases as pharmaceutical data 615, patient data 616, product data 617, patient care protocol or standards of care reference material 618, medical research data 619, or medical websites 620, such as those set up by information vendors or manufacturers. A remote patient information filtering system 613 is an important part of the methods. The filter 613 parses the patient records or physician requests, and generates requests to the various databases which are filtered and do not contain information which is patient-identity-specific. This is to protect patient identity while still being able to access information.

The means for sending information back to professionals and patients includes placing information in a custom web page 610, created for the requester, or sending email responses to professionals or patients to their email addresses 611 and 612. Alternatively, information can be sent directly and with little delay to the devices 601.

In some cases, consumers or patients at home might use the system to communicate data and measurements. Device 601d communicates via the telephone network 606 or data network 607 with a patient care center 605. At the patient care center, voice, data, or measurements can be received via the telephone or data network and analyzed by a human or machine. Responses can be given verbally in real time using a telephone hookup, or sent to the patient via a data network to their email access address 612. The analyst 605 can also take control of the measurement device 601d, in order to control the taking of data.

A proprietary aspect of the invention is the combination of the device with these data networks and databases to form a new method for disseminating and recording information, making a connection between the point of care, and sources of data and information. The uniqueness of the invention lies in the integration of such means to provide point-of-care access to information. The device itself provides user-friendly interfaces, and the system as a whole, as shown in FIG. 5, provides the methods and means for information recording and access.

The invention claimed is:

1. An electronic stethoscope with expanded program execution and communications capability, comprising:
 a portable housing in the physical form of a stethoscope that is wearable around the neck or shoulders of an operator, to house further elements comprising:
 central processing unit;
 nonvolatile digital memory means selected from a group consisting of flash memory, electrically erasable programmable read only memory (EEPROM), and magnetic media;
 one or more software programs, executable by said central processing unit, which expand the functions executed by said stethoscope,
 said functions comprising medical measurement, information processing and communications functions;
 digital communications means;
 wherein said software programs are transferred via said digital communications means, stored in said nonvolatile digital memory means, and executed by said central processing unit.

2. The electronic stethoscope as in claim 1 wherein said digital memory means is physically removable from electronic stethoscope housing.

3. The electronic stroboscope as in claim 1 wherein said digital communication means is a wired cable.

4. The electronic stethoscope as in claim 1 wherein said digital communications means is an infrared optical communications link.

5. The electronic stethoscope as in claim 1 wherein said digital communications means is a wireless communications link.

6. The electronic stethoscope as in claim 1 wherein said digital communications means is a wireless communications means physically removable from said electronic stethoscope housing.

7. The electronic stethoscope as in claim 1 wherein said digital communications means uses an 802.11 communications protocol.

8. The electronic stethoscope as in claim 1 wherein said digital communications means uses an Internet protocol selected from the group consisting of transmission control protocol/Internet protocol (TCP/IP), file transfer protocol (FTP), and point to point protocol (PPP) communications protocols.

9. The electronic stethoscope as in claim 1 wherein said one or more software programs are medical information software programs selected from the group consisting of drug dosage database access software, drug interaction database access software, and medical research database access software.

10. The electronic stethoscope as in claim 9 further comprising a barcode reader operatively connected to said central processing unit such that database reading and writing can be effected by barcode scanner input.

11. The electronic stethoscope as in claim 1 wherein said software includes algorithms for the processing of auscultation sounds.

* * * * *